United States Patent [19]

Ishii et al.

[11] Patent Number: 4,994,790
[45] Date of Patent: Feb. 19, 1991

[54] METHOD FOR SETTING ALARM AND WAVE INDICATING SENSITIVITY

[75] Inventors: Shoji Ishii; Yasuji Yukimitsu, both of Tokyo, Japan

[73] Assignee: Fukuda Denshi Co., Ltd., Tokyo, Japan

[21] Appl. No.: 400,625

[22] Filed: Aug. 30, 1989

[30] Foreign Application Priority Data

Mar. 2, 1989 [JP] Japan ................................ 1-50689
Mar. 2, 1989 [JP] Japan ................................ 1-50690

[51] Int. Cl.$^5$ ........................ G08B 23/00; A61B 5/02
[52] U.S. Cl. ...................................... 340/573; 128/671
[58] Field of Search ............... 340/573; 128/670-671, 128/721-723, 782

[56] References Cited

U.S. PATENT DOCUMENTS 4,115,864  9/1978  Vick et al. .................... 340/573 X Primary Examiner—Glen R. Swann, III
Assistant Examiner—Thomas J. Mullen, Jr.
Attorney, Agent, or Firm—Sughrue, Mion, Zinn, Macpeak & Seas

[57] ABSTRACT

A method for setting an alarm comprising, with the present time value, the upper limit and lower limit of the living body signal being indicated, the operation of setting the threshold of the upper limit or lower limit is carried out depressing the keys indicated, and a method for setting a wave indicating sensitivity comprising, with a plurality of keys for setting sensitivity indicated, depressing any one of the indicated keys.

13 Claims, 6 Drawing Sheets

METHOD FOR SETTING ALARM AND WAVE INDICATING SENSITIVITY

BACKGROUND OF THE INVENTION

1. Field Of The Invention

The present invention relates to a method for setting an alarm and a wave indicating sensitivity. More particularly, it relates to a method for setting an alarm and a wave indicating sensitivity, which are applied to an apparatus for monitoring a patient.

2. Description Of The Related Art

Generally, in an apparatus for monitoring the patient, composed of an electrocardiogram (ECG) central monitor, etc., a method for setting an alarm and a method for setting a wave indicating sensitivity are used respectively.

The method for setting an alarm is as follows. That is to say, when the value at the present time of the living body signal, for example heart rate, of the patient is more than the fixed upper limit or the fixed lower limit, an alarm is sounded. In the prior art, the operation of setting previously the above-mentioned upper and lower limits is carried out by means of volume.

Next, the method for setting a wave indicating sensitivity is as follows. That is to say, when the wave of the living body signal of the patient, for example an electrocardiogram signal, is indicated, the sensitivity thereof can be set.

Ordinarily, in an electrocardiograph, the index of the recorder is adjusted so as to vary by 10 mm, with respect to 1 mV of electromotive force generated by the monitored patient's heart, in which case a wave indicating sensitivity is defined as "1". Thus, when 10 mm along the axis of the ordinate corresponds to 1 mV, the wave indicating sensitivity is 1. Therefore, when 5 mm along the axis of the ordinate corresponds to 1 mV, the wave indicating sensitivity is ½. Moreover, when 20 mm along the axis of the ordinate corresponds to 1 mV, the wave indicating sensitivity is 2.

In the prior art method, the above sensitivity is set by depressing a key several times so as to set the sensitivity to the desired level.

The defects of the aforementioned conventional methods of setting an alarm and a wave indicating sensitivity are as follows.

With respect to the method for setting an alarm, at first, since volume is used, the apparatus must accommodate a suitable device therefor. Hence, the whole apparatus is bigger.

Additionally, since the present time value of the living body signal of the patient is not indicated, it is impossible to set the upper limit or lower limit by referring to an indication of the above-mentioned present time value. Thus, it is difficult to set the upper limit or lower limit.

Moreover, owing to volume, the expense of the apparatus is great.

With respect to the method of setting a wave indicating sensitivity, it takes a great deal of trouble to set sensitivity. For example, it is necessary to repeatedly depress a key for setting sensitivity, as aforementioned.

SUMMARY OF THE INVENTION

An object of the present invention is to provide a method for setting an alarm, in which the alarm setting operation is done easily, the apparatus which employs the method is small, and the cost of utilizing the method is low.

Another object of the present invention is to set easily the wave indicating sensitivity easily.

The above-mentioned first object can be achieved by a method for setting an alarm comprising the steps of indicating the present time value, the upper limit and lower limit of the living body signal and setting the threshold of the upper limit or lower limit by pushing keys indicated.

The above-mentioned second object can be achieved by a method for setting a wave indicating sensitivity comprising the steps of providing a plurality of keys for setting an indicated sensitivity, and setting a wave indicating sensitivity by pushing any one of the keys.

BRIEF DESCRIPTION OF THE DRAWINGS

Further features and advantages of the present invention will be apparent from the ensuing description with reference to the accompanying drawings wherein:

DESCRIPTION OF THE PREFERRED EMBODIMENTS (1) First aspect of the present invention In FIG. 1, reference numeral 10 shows the present time value of the living body signal of one patient, 14 shows the upper limit, 12 shows the lower limit, 14S shows the threshold of the upper limit, and 12S shows the threshold of the lower limit.

Figure 1:
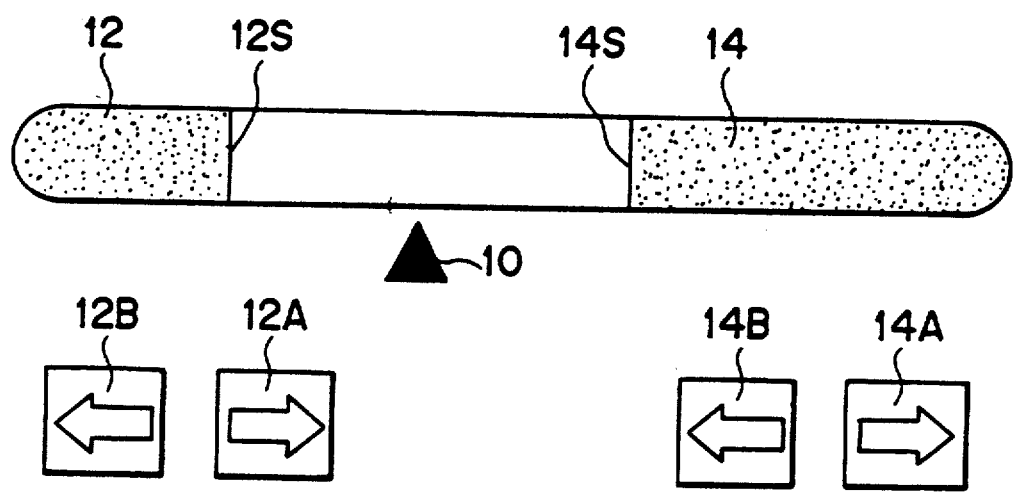
FIG. 1 is a drawing of the first embodiment of the first aspect of the present invention.

Located beneath the present time value 10 are a key 14A for increasing the upper limit 14, a key 14B for decreasing the upper limit 14, a key 12A for increasing the lower limit 12, and a key 12B for decreasing the lower limit 12.

When the key 14A is pushed, the threshold 14S moves to the right (as seen when looking into the drawing), and thereby is increased. When the key 14A is no longer depressed, the threshold 14S stops increasing, whereby the operation of setting the threshold 14S is ended.

When the key 14B is depressed, the threshold 14S moves to the left (as seen when looking into the drawing), and it is decreased. When the key 14B is no longer depressed, the threshold 14S stops decreasing, whereby the operation of setting the threshold 14S is ended.

Since the operation of the keys 12A and 12B are the same as those for keys 14A and 14B, the explanation thereof will be omitted.

Figure 2:
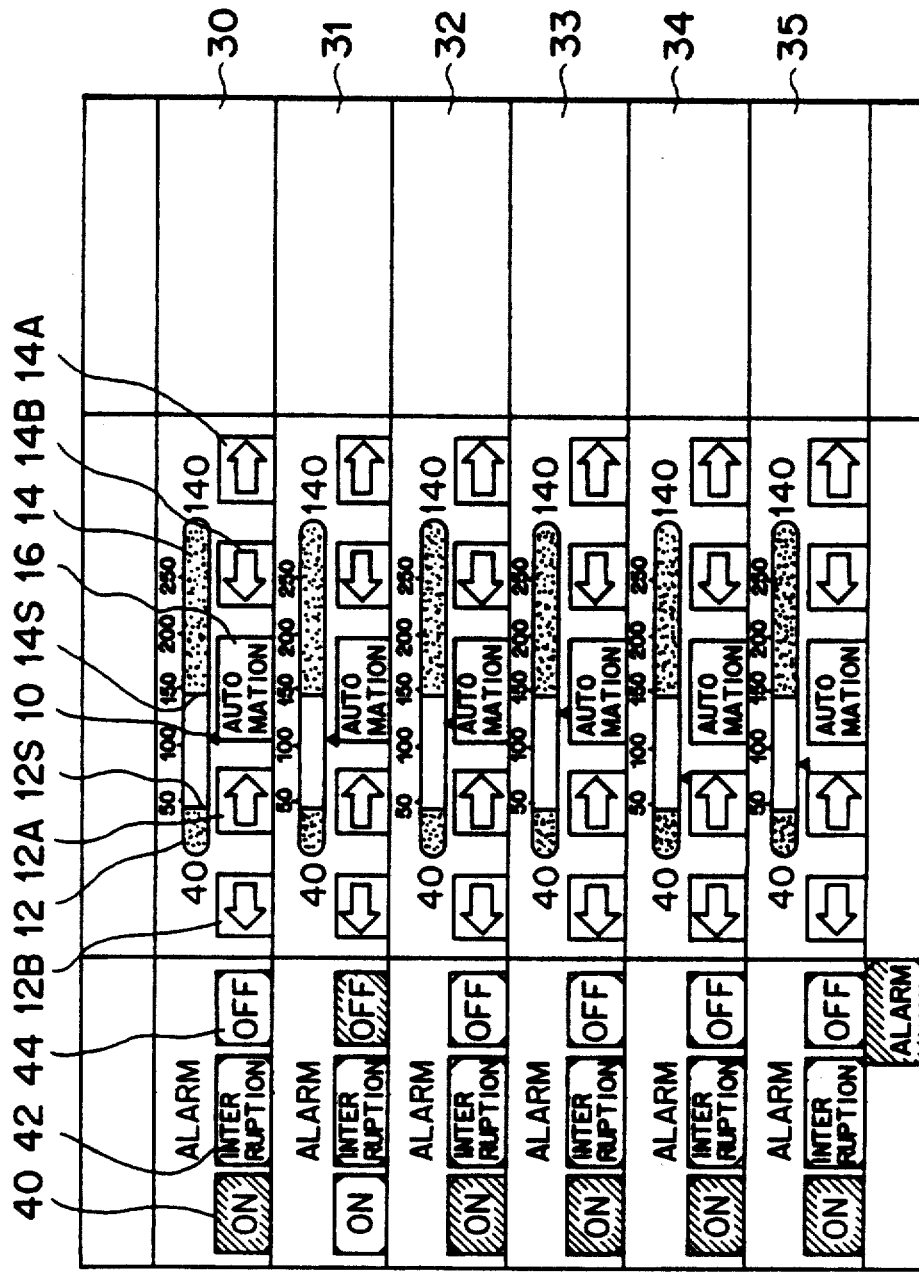
FIG. 2 is a drawing of the second embodiment of the first aspect of the present invention.

FIG. 2 is a drawing of the second embodiment of the first aspect of the present invention. In FIG. 2, an embodiment is disclosed so as to carry out simultaneously in all of the, beds in the appropriate area the operation of setting the alarm, regarding not one patient, but all of the patients.

The picture shown in FIG. 2 is displayed by pushing an alarm key 20 indicated on the lower section of FIG. 2.

When the condition of the patient is normally monitored, the living body signal for example the electrocardiogram signal wave, of each patient in its entirety, is displayed.

However, when the alarm key 20 is depressed, the electrocardiogram wave is compressed and displayed for each patient, respectively on the right side regions 30, 31, 32, 33, 34 and 35, as shown in FIG. 2.

In FIG. 2, the present time value 10 of the living body signal of each patient is the heart rate respectively. As shown in FIG. 2, scales 50, 100 . . . are indicated, as well as a numerical value 140 of the content of the present time upper limit threshold 14S above the key 14A. A numerical value 40 of the content of the present time lower limit threshold 12S is indicated above the key 12B.

The operation of setting an alarm in accordance with the present invention will be explained hereinafter. When the key 14A is depressed simultaneously with viewing the scale, the threshold 14S moves to the right (as seen in viewing FIG. 2 straight-on), and it is increased.

When the key 14A is no longer depressed, at the same time that the threshold 14S reaches the required scale, the threshold 14S stops increasing, whereby the operation of setting the threshold 14S is ended.

When the key 14B is depressed, the threshold 14S moves to the left (as seen when viewing FIG. 2 straight-on), and it decreases.

When the key 14B is no longer depressed, the threshold 14S stops decreasing, and the operation of setting the threshold 14S is ended.

The operation of keys 12A and 12B are the same as those of keys 14A and 14B, as aforementioned.

A key 16, which is indicated respectively on the central portion of the picture, is a key for setting automatically the upper limit or lower limit.

When the key 16 is pushed, the alarm may be set automatically so that the threshold 14S is $+x\%$ or the threshold 12S is $-y\%$, with respect to the present time value 10.

On the left side of FIG. 2, a key 40 for switching on the alarm, a key 42 for interrupting the alarm, and a key 44 for switching off the alarm are provided, respectively, for each patient.

When the key 40 is pushed for an appropriate patient, the alarm is indicated as "ON" for the patient. When the key 42 is pushed, the alarm is indicated as being interrupted for a required time. When the key 44 is pushed, the alarm indication is switched off.

Figure 3:
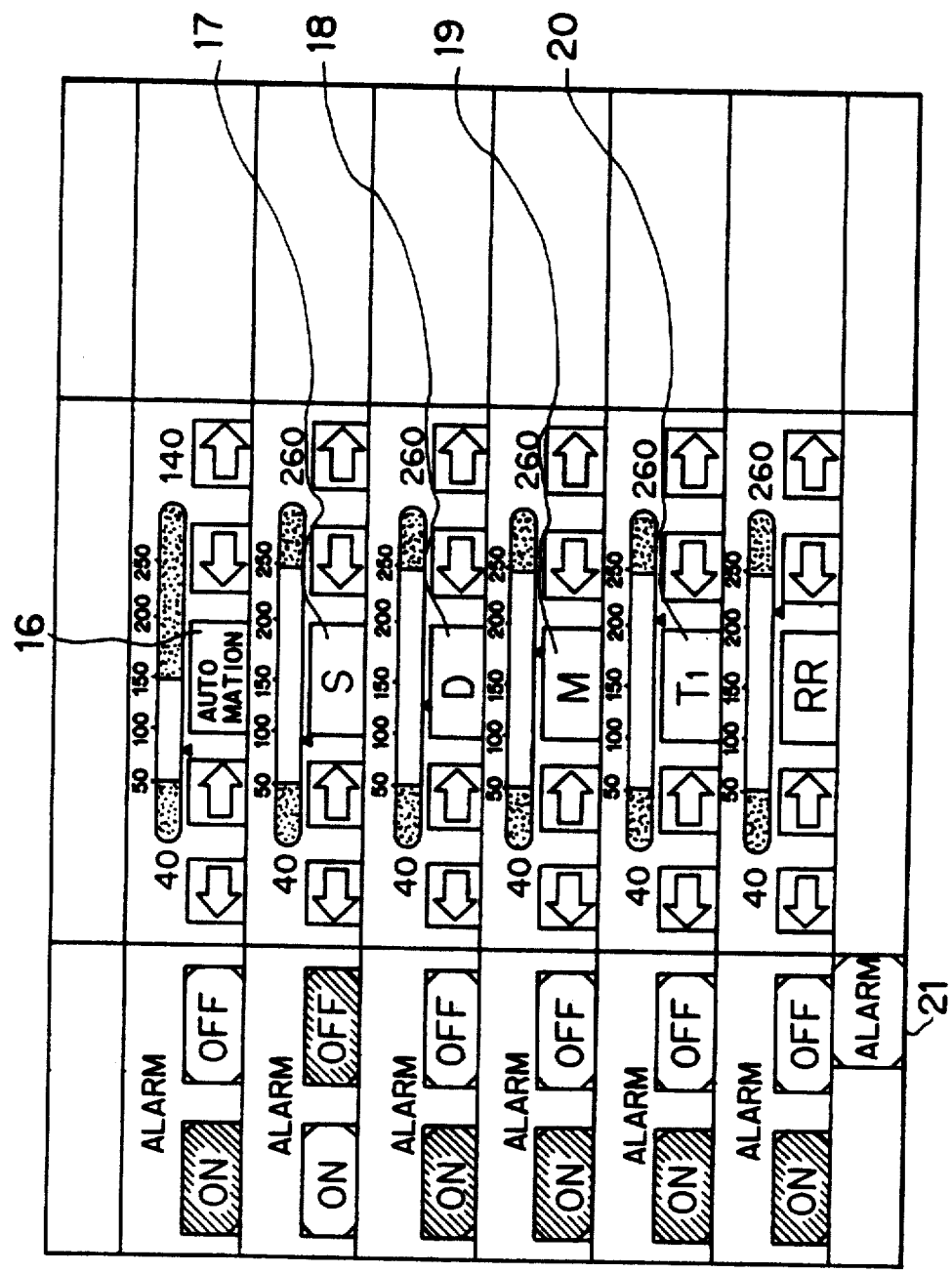
FIG. 3 is a drawing of the third embodiment of the first aspect of the present invention.

FIG. 3 is a drawing of the third embodiment of the first aspect of the present invention, and shows the case wherein the operation of setting an alarm is carried out simultaneously with respect to all the parameters of one patient, i.e., all the living body signals including heart rate, blood pressure, and bodily temperature, etc.

In FIG. 3, for example, the operation of setting an alarm may be carried out simultaneously in order from top to bottom, with respect to the parameters of heart rate, blood pressure 1, blood pressure 2, blood pressure 3, bodily temperature, and respiration rate.

Since the operation of setting an alarm in the embodiment of FIG. 3 is almost the same as that of FIG. 2, only the differences will be described hereinafter.

With respect to the heart rate, the alarm may be set automatically by pushing a key 16. With respect to the remaining parameters (blood pressure 1 through the respiration rate), a set item also may be verified for each parameter, and the alarm can be set regarding the set item.

For example, with respect to the blood pressure 1, when a key 17 is depressed, a set item is verified so that S (meaning contraction) D (meaning extension), and M (meaning average) appear in order. Regarding each set item verified, the alarm may be set by the same operation as shown in the embodiment of FIG. 2.

With respect to the blood pressure 2, blood pressure 3, bodily temperature, respiration rate, the alarm can be set in the same manner as that of the blood pressure 1.

As aforementioned, according to the first aspect of the present invention, a method for setting an alarm is provided wherein the present time value, the upper limit and lower limit of the living body signal are indicated, and the operation of setting the threshold of the upper limit or lower limit is carried out by pushing the appropriate key indicated.

Thus, since the present time value, upper limit, and lower limit of the living body signal are indicated, the upper limit or lower limit is set by looking at the above-mentioned indicated values. Therefore, the operation of setting an alarm can be carried out very easily.

Additionally, since there is no volume, the first aspect of the present invention has another effect in that the apparatus is not complicated and that the cost of the whole apparatus is low.

(2) Second aspect of the present invention.

Figure 4:
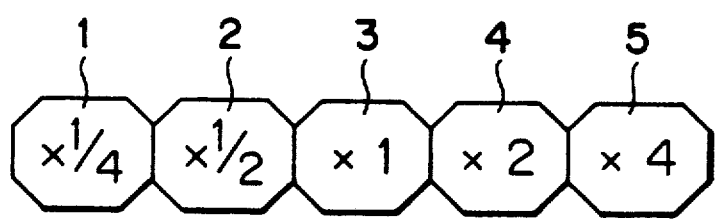
FIG. 4 is a drawing of the first embodiment of the second aspect of the present invention.

FIG. 4 is a drawing of the first embodiment of the second aspect of the present invention, wherein reference numerals 1 to 5 show keys for setting a wave indicating sensitivity, respectively. The embodiment of FIG. 4 is the case where a wave indicating sensitivity of one living body signal of one patient, for example an electrocardiogram signal, is set.

Keys 1, 2, 3, 4, and 5 are used when wave indicating sensitivities are set to ¼, ½, 1, 2, and 4, respectively.

Figure 5:
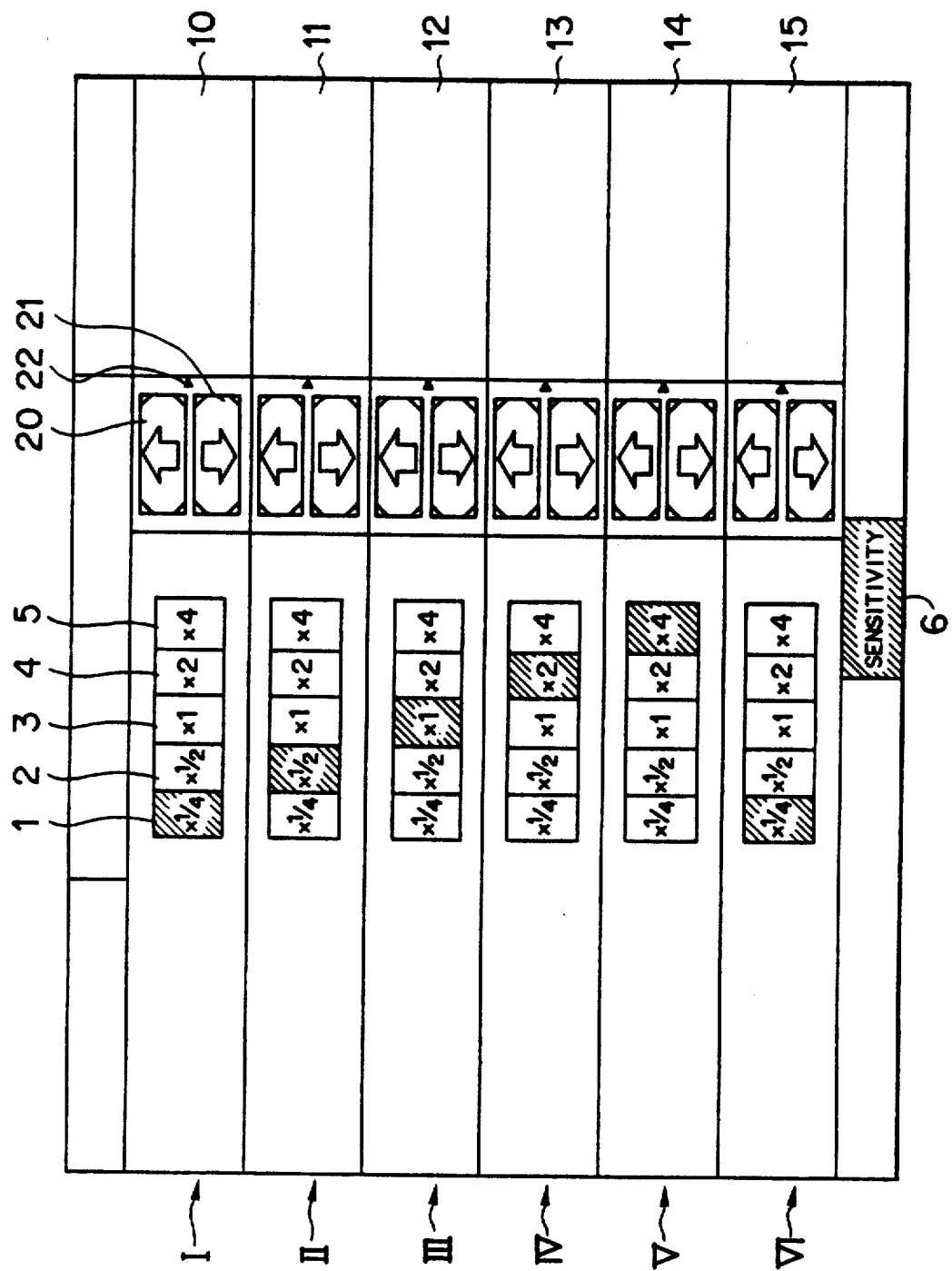
FIG. 5 is a drawing of the second embodiment of the second aspect of the present invention.

According to the second aspect of the present invention, when any one of the above indicated keys 1 to 5 is pushed, a wave indicating sensitivity may be set with one operation. FIG. 5 is a drawing of the second embodiment of the second aspect of the invention, in which a wave indicating sensitivity is set simultaneously, regarding all the beds (i.e., all patients to be monitored).

In FIG. 5, keys 1 to 5 are shown for each of the beds I, II, III . . . VI.

In regions 10, 11 . . . 15 on the right side of the keys 1 to 5, the wave objected to sensitivity, for example, the wave of the electrocardiogram signal are indicated, respectively.

Each bed, when the keys 1, 2, 3, 4, and 5 are depressed, the sensitivities of the waves become ¼, ½, 1, 2 and 4, respectively.

By pushing the wave of the basic picture, wave indicating sensitivity may be set in order in a direction from a small sensitivity to a large sensitivity or from a large sensitivity to a small sensitivity.

Alternatively, they may be in order cyclically, from the smallest sensitivity to the largest sensitivity or from the largest sensitivity to the smallest sensitivity.

In FIG. 5, keys 20 and 21 for setting the position of the wave are indicated beside keys 1 to 5 and the wave in the regions 10 to 15 of the appropriate bed.

The keys 20 and 21 are those for increasing or decreasing respectively the position of the wave in the regions 10 to 15. That is to say, when the key 20 is depressed, the wave increases, and when the key 21 is depressed, the wave decreases. Reference numeral 22 shows the present time position of the wave.

The operation of the second aspect of the invention will be described hereinafter, based on FIG. 5. First, in the basic picture, a sensitivity key 6 is depressed. Thereby, the keys 1 to 5 are indicated simultaneously in all the beds I to VI, and the waves of the electrocardiogram signals are indicated in the regions 10 to 15, as shown in FIG. 5.

With respect to the bed I, as shown in oblique lines, when the key 1 is depressed, a wave indicating sensitivity becomes $\frac{1}{4}$. With respect to the beds II to VI, when keys 2, 3, 4, 5 and 1 are depressed, the wave indicating sensitivity becomes $\frac{1}{2}$, 1, 2, 4 and $\frac{1}{4}$, respectively.

Therefore, when only the sensitivity key 6 is depressed, a plurality of keys 1 to 5 are indicated simultaneously for all of the beds, and when any one of the keys 1 to 5 are depressed, a wave indicating sensitivity may be set.

Next, the operation of the keys 20 and 21 will be described hereinafter. For example, with respect to the bed 1, the present time wave position 22 appears as shown in FIG. 5. Hence, if the entire wave is to be decreased, the key 21 may be depressed. Alternatively, if the entire wave is to be increased, the key 20 may be depressed. Thus, with the provision of the keys 20 and 21, the wave with set sensitivity can be observed very easily.

With respect to the other beds II, III . . . VI, the operations of wave position setting keys are the same as that for the bed I.

Figure 6:
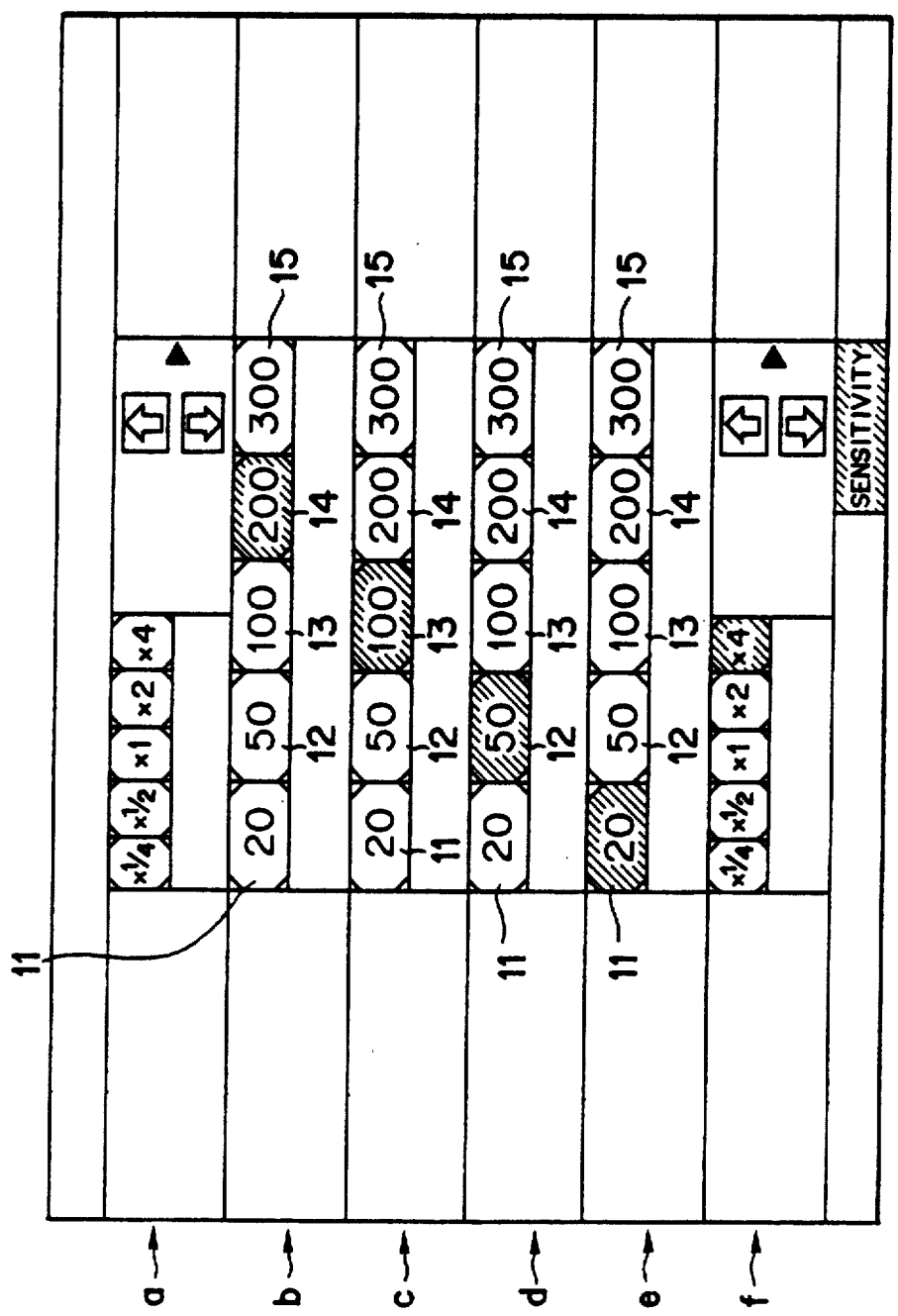
FIG. 6 is a drawing of the third embodiment of the second aspect of the present invention.

FIG. 6 is a drawing of the third embodiment of the second aspect of the present invention, and has a wave indicating sensitivity set simultaneously regarding all the parameters of one patient, that is to say, the living body signals relating to one electrocardiogram of the patient, blood pressure and bodily temperature etc.

In FIG. 6, for example, with respect to the parameters of the electrocardiogram shown in reference letter a, the blood pressure 1 shown in b, the blood pressure 2 shown in c, the blood pressure 3 shown in d, the blood pressure 4 shown in e, and the respiration number shown in f, a wave indicating sensitivity may be set simultaneously.

The operation of setting sensitivity of the electrocardiogram a and the respiration rate f is the same as that of FIG. 5. On the other hand, the operation of setting the sensitivity of the blood pressures 1 to 4 is as follows.

That is to say, when keys 14, 13, 12, and 11 are depressed as shown in oblique lines, the sensitivities of 200 mmHg, 100 mmHg, 50 mmHg, and 20 mmHg may be set respectively with one operation.

As aforementioned, according to the second aspect of the present invention, a method for setting a wave indicating sensitivity is provided, wherein a plurality of keys for setting sensitivity are indicated, and a wave indicating sensitivity is set by any one of the indicated keys.

Hence, when any one of a plurality of keys for setting sensitivity is depressed, a wave indicating sensitivity may be set with one operation.

Therefore, with the second aspect of the present invention, the operation of setting sensitivity can be carried out very easily.

What is claimed is:

1. A method for setting an alarm in an apparatus for monitoring a plurality of patients, having a keyboard with a plurality of keys, said method comprising the steps of:
   indicating the present time value, the upper limit and lower limit of a living body signal of one of said patients; and
   setting a threshold of the upper limit and the lower limit based upon the present time value of said living body signal by depressing appropriate ones of said keys.

2. A method for setting an alarm according to claim 1, wherein said indicating step is performed simultaneously for all of a plurality of patients.

3. A method for setting an alarm according to claim 1, wherein said indicating step is performed simultaneously regarding all of a plurality of parameters of each of said plurality of patients.

4. A method for setting an alarm according to claim 1, wherein said keys comprise a key for increasing the upper limit, a key for decreasing the upper limit, a key for increasing the lower limit, and a key for decreasing the lower limit.

5. A method for setting an alarm according to claim 1, wherein said step of setting the threshold may be performed automatically by depressing a key for setting automatically the upper limit and a key for setting automatically the lower limit of said living body signal.

6. A method for setting an alarm according to claim 1, wherein an indication of said alarm may be one of switched on and switched off.

7. A method for setting an alarm according to claim 1, wherein an indication of said alarm may be interrupted for a required time.

8. A method for setting a wave indicating sensitivity in an apparatus for monitoring a plurality of patients, having a keyboard with a plurality of keys, said method comprising the step of:
   setting a wave indicating sensitivity by depressing any one of a plurality of indicated keys.

9. A method for setting a wave indicating sensitivity according to claim 8, wherein said setting step may be performed simultaneously for all of said plurality of patients.

10. A method for setting a wave indicating sensitivity according to claim 8, wherein said setting step may be performed simultaneously regarding all of a plurality of parameters of each of said plurality of patients.

11. A method for setting a wave indicating sensitivity according to claim 8, wherein said method further comprises a step of setting a position of the wave.

12. A method for setting a wave indicating sensitivity according to claim 8, wherein said setting step is performed sequentially in a direction in one of from a small sensitivity to a large sensitivity and from said large sensitivity to said small sensitivity, by depressing an appropriate one of said plurality of keys.

13. A method for setting a wave indicating sensitivity according to claim 8, wherein said setting step is performed in order cyclically, by one of from a small sensitivity to a large sensitivity and from said large sensitivity to said small sensitivity, by depressing an appropriate one of said plurality of keys.

* * * * *